United States Patent
Doyle et al.

(10) Patent No.: US 10,328,202 B2
(45) Date of Patent: Jun. 25, 2019

(54) METHODS AND SYSTEMS FOR DETERMINING FLUID ADMINISTRATION

(71) Applicant: Covidien LP, Mansfield, MA (US)

(72) Inventors: Peter Doyle, Vista, CA (US); Paul S. Addison, Edinburgh (GB); James N. Watson, Dunfermline (GB)

(73) Assignee: Covidien LP, Mansfield, MA (US)

( * ) Notice: Subject to any disclaimer, the term of this patent is extended or adjusted under 35 U.S.C. 154(b) by 597 days.

(21) Appl. No.: 15/006,018

(22) Filed: Jan. 25, 2016

(65) Prior Publication Data

US 2016/0220756 A1 Aug. 4, 2016

Related U.S. Application Data

(60) Provisional application No. 62/112,052, filed on Feb. 4, 2015.

(51) Int. Cl.
*A61M 5/172* (2006.01)
*A61B 5/08* (2006.01)
(Continued)

(52) U.S. Cl.
CPC .............. *A61M 5/1723* (2013.01); *A61B 5/08* (2013.01); *A61B 5/14551* (2013.01);
(Continued)

(58) Field of Classification Search
CPC .. A61M 5/1723; A61B 5/4875; A61B 5/4848; A61B 5/08; A61B 5/02416; A61B 5/0816
See application file for complete search history.

(56) References Cited

U.S. PATENT DOCUMENTS

| 4,781,195 A | 11/1988 | Martin |
| 4,846,183 A | 7/1989 | Martin |

(Continued)

FOREIGN PATENT DOCUMENTS

| WO | WO 1998/51212 | 11/1998 |
| WO | WO 2011/041090 | 4/2011 |
| WO | WO 2014/166504 | 10/2014 |

OTHER PUBLICATIONS

Challoner, A.V.J., Photoelectric Plethysmography for Estimating Cutaneous Blood Flow, in "Non-Invasive Physiological Measurements," Rolfe, P., Academic Press Inc., London, 1979, pp. 125-151.
(Continued)

*Primary Examiner* — Bradley J Osinski
(74) *Attorney, Agent, or Firm* — Shumaker & Sieffert, P.A.

(57) ABSTRACT

Methods and systems are provided for determining fluid administration. The system may determine fluid administration based on the fluid responsiveness and regional oxygen saturation of a subject. The system may receive the fluid responsiveness and regional oxygen saturation from external sources or may determine one or both based on received physiological signals. In some embodiments, the system may determine whether to administer fluid based on the fluid responsiveness and regional oxygen saturation. In some embodiments, the system may determine the amount of fluid to administer based on the fluid responsiveness and regional oxygen saturation. In some embodiments, the system may determine the effectiveness of fluid administration. In some embodiments, the system may provide an indication of the determined fluid administration so that a care-giver can implement the appropriate fluid administration. In some embodiments, the system may control the fluid administration based on its determination.

20 Claims, 7 Drawing Sheets

(51) Int. Cl.
*A61B 5/1455* (2006.01)
*A61B 5/00* (2006.01)
*A61B 5/024* (2006.01)

(52) U.S. Cl.
CPC .......... *A61B 5/4848* (2013.01); *A61B 5/4875* (2013.01); *A61B 5/02416* (2013.01); *A61B 5/02438* (2013.01); *A61B 5/0816* (2013.01)

(56) References Cited

U.S. PATENT DOCUMENTS

| | | |
|---|---|---|
| 4,942,877 A | 7/1990 | Sakai et al. |
| 5,115,133 A | 5/1992 | Knudson |
| 5,152,296 A | 10/1992 | Simons |
| 5,187,672 A | 2/1993 | Chance et al. |
| 5,222,495 A | 6/1993 | Clarke et al. |
| 5,253,646 A | 10/1993 | Delpy et al. |
| 5,267,562 A | 12/1993 | Ukawa et al. |
| 5,273,036 A | 12/1993 | Kronberg et al. |
| 5,277,181 A | 1/1994 | Mendelson et al. |
| 5,299,570 A | 4/1994 | Hatschek |
| 5,343,818 A | 9/1994 | McCarthy et al. |
| 5,355,882 A | 10/1994 | Ukawa et al. |
| 5,419,321 A | 5/1995 | Evans |
| 5,440,388 A | 8/1995 | Erickson |
| 5,482,034 A | 1/1996 | Lewis et al. |
| 5,564,417 A | 10/1996 | Chance |
| 5,661,302 A | 8/1997 | Evans et al. |
| 5,673,701 A | 10/1997 | Chance |
| 5,747,806 A | 5/1998 | Khalil et al. |
| 5,770,454 A | 6/1998 | Essenpreis et al. |
| 5,803,910 A | 9/1998 | Potratz |
| 5,820,558 A | 10/1998 | Chance |
| 5,825,488 A | 10/1998 | Kohl et al. |
| 5,830,132 A | 11/1998 | Robinson |
| 5,902,235 A | 5/1999 | Lewis et al. |
| 5,954,053 A | 9/1999 | Chance et al. |
| 5,983,122 A | 11/1999 | Jarman et al. |
| 6,058,324 A | 5/2000 | Chance |
| 6,064,898 A | 5/2000 | Aldrich |
| 6,122,535 A | 9/2000 | Kaestle et al. |
| 6,129,675 A | 10/2000 | Jay |
| 6,236,047 B1 | 5/2001 | Malin et al. |
| 6,278,889 B1 | 8/2001 | Robinson |
| 6,353,226 B1 | 3/2002 | Khalil et al. |
| 6,361,501 B1 | 3/2002 | Amano et al. |
| 6,434,408 B1 | 8/2002 | Heckel |
| 6,438,399 B1 | 8/2002 | Kurth |
| 6,549,795 B1 | 4/2003 | Chance |
| 6,553,242 B1 | 4/2003 | Sarussi |
| 6,594,513 B1 | 7/2003 | Jobsis et al. |
| 6,615,061 B1 | 9/2003 | Khalil et al. |
| 6,615,064 B1 | 9/2003 | Aldrich |
| 6,615,065 B1 | 9/2003 | Barrett et al. |
| 6,701,170 B2 | 3/2004 | Stetson |
| 6,702,752 B2 * | 3/2004 | Dekker .............. A61B 5/02416 600/479 |
| 6,708,048 B1 | 3/2004 | Chance |
| 6,709,402 B2 | 3/2004 | Dekker |
| 6,773,397 B2 | 8/2004 | Kelly |
| 6,801,798 B2 | 10/2004 | Geddes et al. |
| 6,819,950 B2 | 11/2004 | Mills |
| 6,829,496 B2 | 12/2004 | Nagai et al. |
| 6,839,582 B2 | 1/2005 | Heckel |
| 6,839,659 B2 | 1/2005 | Tarassenko et al. |
| 7,044,917 B2 | 5/2006 | Arnold |
| 7,098,037 B2 | 8/2006 | Haas et al. |
| 7,187,960 B2 | 3/2007 | Abreu |
| 7,271,912 B2 | 9/2007 | Sterling et al. |
| 7,315,752 B2 | 1/2008 | Kraemer et al. |
| 7,356,365 B2 | 4/2008 | Schurman |
| 7,424,317 B2 | 9/2008 | Parker et al. |
| 7,976,472 B2 | 7/2011 | Kiani |
| 8,221,319 B2 | 7/2012 | Lovejoy |
| 8,251,912 B2 | 8/2012 | Shelley et al. |
| 8,298,151 B2 | 10/2012 | Riobo Aboy et al. |
| 8,414,499 B2 | 4/2013 | Al-Ali et al. |
| 8,529,458 B2 | 9/2013 | Kim et al. |
| 8,532,754 B2 | 9/2013 | Cannesson |
| 8,551,005 B2 | 10/2013 | Baruch |
| 8,821,397 B2 | 9/2014 | Al-Ali et al. |
| 8,965,472 B2 | 2/2015 | Benni |
| 9,326,712 B1 | 5/2016 | Kiani |
| 2003/0236647 A1 | 12/2003 | Yoon et al. |
| 2004/0059210 A1 | 3/2004 | Stetson |
| 2004/0122300 A1 | 6/2004 | Boas et al. |
| 2004/0186358 A1 | 9/2004 | Chernow et al. |
| 2008/0228053 A1 | 9/2008 | Wang et al. |
| 2009/0048527 A1 | 2/2009 | Hatib et al. |
| 2009/0326353 A1 | 12/2009 | Watson et al. |
| 2010/0240964 A1 * | 9/2010 | Sterling ............. A61B 5/14532 600/300 |
| 2010/0324827 A1 | 12/2010 | Addison et al. |
| 2011/0208024 A1 | 8/2011 | Widman et al. |
| 2011/0270097 A1 | 11/2011 | Aboy et al. |
| 2012/0053433 A1 | 3/2012 | Chamoun et al. |
| 2012/0179007 A1 * | 7/2012 | Rinehart ................ A61B 5/029 600/301 |
| 2012/0296219 A1 | 11/2012 | Chon et al. |
| 2014/0058229 A1 | 2/2014 | Su et al. |
| 2014/0073889 A1 | 3/2014 | Su et al. |
| 2014/0316278 A1 | 10/2014 | Addison et al. |
| 2014/0371548 A1 | 12/2014 | Al-Ali et al. |
| 2015/0099950 A1 | 4/2015 | Al-Ali et al. |

OTHER PUBLICATIONS

Dorlas, J.C. and Nijboer, J.A., "Photo-Electric Plethysmography as a Monitoring Device in Anesthesia. Application and Interpretation," British Journal of Anesthesia, 1985; 57(5), pp. 524-530.

Michard, Frederic, et al., "Clinical use of Respiratory Changes in Arterial Pulse Pressure to Monitor the Hemodynamic Effects of PEEP," Am J Respir Crit Care Med, Mar. 1999; 159(3), pp. 935-939.

Partridge, Brian L., "Use of Pulse Oximetry as a Noninvasive Indicator of Intravascular Volume Status," Journal of Clinical Monitoring, Oct. 1987; 3(4), pp. 263-268.

Shamir, M., et al., "Pulse Oximetry Plethysmographic Waveform During Changes in Blood Volume," British Journal of Anesthesia, 1999; 82(2), pp. 178-181.

Futier et al., "Use of Near-Infrared Spectroscopy During a Vascular Occlusion Test to Assess the Microcirculatory Response During Fluid Challenge," Critical Care, Sep. 16, 2011, 15(5), pp. 1-10.

Chien et al., "Effects of Fluid Resuscitation on Cerebral Tissue Oxygenation Changes in a Piglet Model of Hemorrhagic Shock," Journal of the Chinese Medical Association, vol. 74, Oct. 2011, pp. 448-454.

Lipcsey et al., "Near Infrared Spectroscopy (NIRS) of the Thenar Eminence in Anesthesia and Intensive Care," Annals of Intensive Care, May 2012, 2(11), pp. 1-9.

Mesquida et al., "Skeletal Muscle Oxygen Saturation (StO2) Measured by Near-Infrared Spectroscopy in the Critically Ill Patients," BioMed Research International, vol. 2013, Article ID 502194, Aug. 21, 2013, pp. 1-8.

* cited by examiner

METHODS AND SYSTEMS FOR DETERMINING FLUID ADMINISTRATION

CROSS-REFERENCE TO RELATED APPLICATION

The present disclosure claims priority to U.S. Provisional Application No. 62/112,052, filed Feb. 4, 2015, which is hereby incorporated by reference herein in its entirety.

SUMMARY

The present disclosure relates to determining fluid administration for a subject, and more particularly relates to determining fluid administration for a subject based on a value indicative of fluid responsiveness and a value indicative of regional oxygen saturation of the subject.

The present disclosure provides embodiments for a physiological monitoring system comprising a light detecting sensor and a processor. The light detecting sensor is configured to detect at least one wavelength of light absorbed through tissue of a subject and generate at least one physiological signal based on the detected at least one wavelength of light. The processor is coupled to the light detecting sensor and is configured to receive the at least one physiological signal, determine a value indicative of fluid responsiveness of the subject based on the at least one physiological signal, receive a value indicative of regional oxygen saturation in a region of the subject's tissue, and determine whether to administer fluid to the subject based on the value indicative of regional oxygen saturation and the value indicative of fluid responsiveness.

The present disclosure provides embodiments for a physiological monitoring system. The system comprises an input configured to receive a plurality of physiological signals, wherein the plurality of physiological signals are indicative of light absorbed by the subject. The system further comprises a saturation calculator, coupled to the input, and configured to calculate regional oxygen saturation in a region of the subject's tissue based on at least two of the plurality of physiological signals. The system further comprises a fluid responsiveness calculator, coupled to the input, and configured to calculate a parameter indicative of fluid responsiveness based on at least one of the plurality of physiological signals. The system further comprises a fluid administration calculator configured to provide an indication regarding the administration of fluid to the subject based on the regional oxygen saturation and the parameter indicative of fluid responsiveness.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
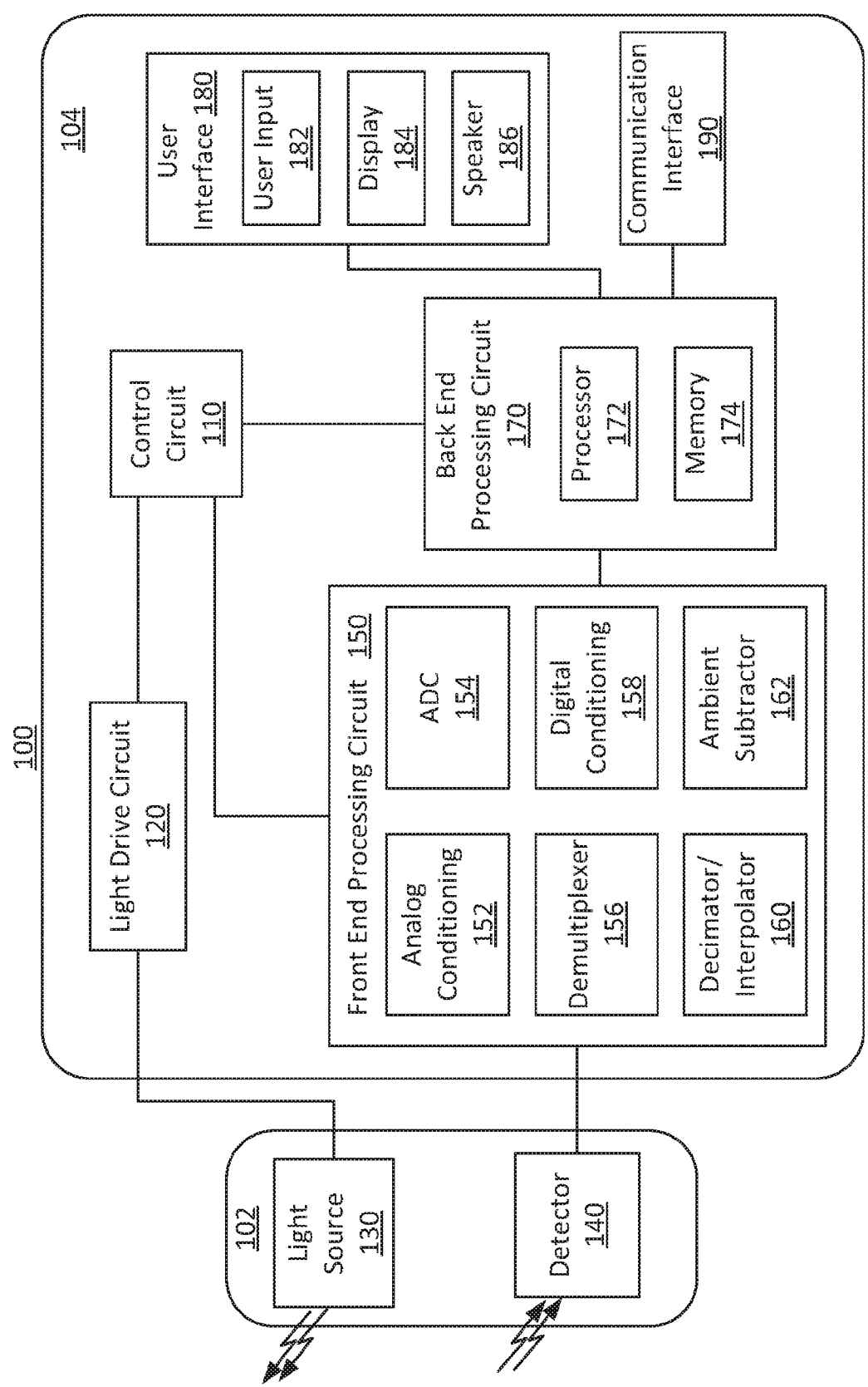
FIG. 1 shows a block diagram of an illustrative physiological monitoring system in accordance with some embodiments of the present disclosure.

The present disclosure is directed towards determining fluid administration for a subject. In one embodiment, a monitor is configured to determine fluid administration for a subject based on a fluid responsiveness parameter and a regional oxygen saturation value of the subject.

Fluid is commonly delivered to a patient in order to improve the patient's hemodynamic status. Fluid is delivered with the expectation that it will increase the patient's cardiac preload, right ventricular end-diastolic volume, left ventricular end-diastolic volume, stroke volume, and cardiac output, resulting in improved oxygen delivery to the organs and tissue. Fluid delivery may also be referred to as volume expansion, fluid therapy, fluid challenge, or fluid loading. However, improved hemodynamic status is not always achieved by fluid loading. Moreover, inappropriate fluid loading may worsen a patient's status, such as by causing hypovolemia to persist (potentially leading to inadequate organ perfusion), or by causing hypervolemia (potentially leading to peripheral or pulmonary edema).

Respiratory variation in the arterial blood pressure waveform is known to be a good predictor of a patient's response to fluid loading, or fluid responsiveness. Fluid responsiveness represents a prediction of whether such fluid loading will improve blood flow within the patient. Fluid responsiveness refers to the response of stroke volume or cardiac output to fluid administration. A patient is said to be fluid responsive if fluid loading does accomplish improved blood flow, such as by an improvement in cardiac output or stroke volume index by about 15% or more. In particular, the pulse pressure variation (PPV) parameter from the arterial blood pressure waveform has been shown to be a good predictor of fluid responsiveness. This parameter can be monitored while adding fluid incrementally, until the PPV value indicates that the patient's fluid responsiveness has decreased, and more fluid will not be beneficial to the patient. This treatment can be accomplished without needing to calculate blood volume or cardiac output directly. This approach, providing incremental therapy until a desired target or endpoint is reached, may be referred to as goal-directed therapy (GDT).

However, determining the PPV is an invasive procedure, requiring the placement of an arterial line in order to obtain the arterial blood pressure waveform. This invasive procedure is time-consuming and presents a risk of infection to the patient. Respiratory variation in a photoplethysmograph (PPG) signal may provide a non-invasive alternative to PPV. The PPG signal can be obtained non-invasively, such as from a pulse oximeter. One measure of respiratory variation in the PPG is the Delta POP metric, which is a measure of the strength of respiratory-induced amplitude modulations of the PPG. This metric assesses changes in the pulse oximetry plethysmograph, and is abbreviated as ΔPOP or DPOP. In addition to DPOP, a number of other measures of respiratory variation may be used to determine fluid responsiveness, including other measures of respiratory-induced amplitude modulations, other respiratory-induced modulations, and any suitable combination thereof. While there is a favorable correlation between DPOP and PPV, there is a need for a more specific and sensitive administration of fluid.

Monitoring regional tissue oxygen saturation using near-infrared spectroscopy (NIRS) can be useful in critically ill patients. It is thus desirable to determine the course of fluid administration based on both a fluid responsiveness parameter such as DPOP and a regional tissue oxygen saturation of a subject. In accordance with some embodiments of the present disclosure, DPOP may be calculated, regional tissue oxygen saturation may be determined or otherwise received, and fluid may be administered based thereon. Such techniques may provide more specific and sensitive administration of fluid and result in end-point improvements in the ultimate GDT of improving tissue oxygenation.

The foregoing techniques may be implemented in an oximeter. An oximeter is a medical device that may determine the oxygen saturation of an analyzed tissue. One common type of oximeter is a pulse oximeter, which may non-invasively measure the oxygen saturation of a patient's blood (as opposed to measuring oxygen saturation invasively by analyzing a blood sample taken from the patient). Another common type of oximeter is a regional oximeter. A regional oximeter is used to estimate the blood oxygen saturation in a region of a subject's tissue. The regional oximeter may compute a differential absorption value for each of two or more wavelengths of light received at two different locations on the subject's body to estimate the regional blood oxygen saturation of hemoglobin in a region of the subject's tissue. For each wavelength of light, the regional oximeter may compare the amount of light absorbed by the subject's tissue in a first region to the amount of light absorbed by the subject's tissue in a second region to derive the differential absorption values. As opposed to pulse oximetry, which typically examines the oxygen saturation of pulsatile, arterial tissue, regional oximetry examines the oxygen saturation of blood in a region of tissue, which may include blood in the venous, arterial, and capillary systems. For example, a regional oximeter may include a sensor unit configured for placement on a subject's forehead and may be used to estimate the blood oxygen saturation of a region of tissue beneath the sensor unit (e.g., cerebral tissue). Oximeters may be included in patient monitoring systems that measure and display various blood characteristics including, for example, blood oxygen saturation (e.g., arterial, venous, regional, or a combination thereof). Such patient monitoring systems, in accordance with the present disclosure, may also measure and display additional or alternative physiological parameters such as pulse rate, respiration rate, respiration effort, blood pressure, hemoglobin concentration (e.g., oxygenated, deoxygenated, and/or total), cardiac output, fluid responsiveness parameters, any other suitable physiological parameters, or any combination thereof.

An oximeter may include a light sensor that is placed at a site on a subject. For example, the light sensor may be placed on a fingertip, toe, forehead or earlobe, or in the case of a neonate, across a foot or hand. The light sensor may also be placed at any other suitable location on a subject. The oximeter may use a light source to pass light through blood perfused tissue and photoelectrically sense the absorption of the light in the tissue. The oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, an inverted signal, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters.

In some embodiments, the photonic signal interacting with the tissue is of one or more wavelengths that are attenuated by the blood in an amount representative of the blood constituent concentration. Red and infrared (IR) wavelengths may be used because it has been observed that highly oxygenated blood will absorb relatively less red light and more IR light than blood with a lower oxygen saturation. By comparing the intensities of two wavelengths at different points in the pulse cycle, it is possible to estimate the blood oxygen saturation of hemoglobin in arterial blood.

The system may process data to determine physiological parameters using techniques well known in the art. For example, the system may determine arterial blood oxygen saturation using two wavelengths of light and a ratio-of-ratios calculation. As another example, the system may determine regional blood oxygen saturation using two wavelengths of light and two detectors located at different distances from the emitters. The system also may identify pulses and determine pulse amplitude, respiration, respiratory variation, fluid responsiveness, blood pressure, other suitable parameters, or any combination thereof, using any suitable calculation techniques. In some embodiments, the system may use information from external sources (e.g., tabulated data, secondary sensor devices) to determine physiological parameters.

It will be understood that the techniques described herein are not limited to oximeters and may be applied to any suitable physiological monitoring device.

FIG. 1 shows a block diagram of illustrative physiological monitoring system 100 in accordance with some embodiments of the present disclosure. System 100 may include a sensor 102 and a monitor 104 for generating and processing sensor signals that include physiological information of a subject. In some embodiments, sensor 102 and monitor 104 may be part of an oximeter. In some embodiments, system 100 may include more than one sensor 102.

Sensor 102 of physiological monitoring system 100 may include light source 130 and detector 140. Light source 130 may be configured to emit photonic signals having one or more wavelengths of light (e.g. red and IR) into a subject's tissue. For example, light source 130 may include a red light emitting light source and an IR light emitting light source, e.g. red and IR light emitting diodes (LEDs), for emitting light into the tissue of a subject to generate sensor signals that include physiological information. In one embodiment, the red wavelength may be between about 600 nm and about 750 nm, and the IR wavelength may be between about 800 nm and about 1000 nm. It will be understood that light source 130 may include any number of light sources with any suitable characteristics. In embodiments where an array of sensors is used in place of single sensor 102, each sensor may be configured to emit a single wavelength. For example, a first sensor may emit only a red light while a second may emit only an IR light.

It will be understood that, as used herein, the term "light" may refer to energy produced by radiative sources such as electromagnetic radiative sources and may include, for example, any wavelength within the radio, microwave, millimeter wave, infrared, visible, ultraviolet, gamma ray or X-ray spectra. Detector 140 may be chosen to be specifically sensitive to the chosen targeted energy spectrum of light source 130.

In some embodiments, detector 140 may be configured to detect the intensity of light at the red and IR wavelengths. In some embodiments, an array of sensors may be used and each sensor in the array may be configured to detect an intensity of a single wavelength. In operation, light may enter detector 140 after passing through the subject's tissue. Detector 140 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detector 140. After converting the received light to an electrical signal, detector 140 may send the detection signal to monitor 104, where the detection signal may be processed and physiological parameters may be determined. In some embodiments, the detection signal may be preprocessed by sensor 102 before being transmitted to monitor 104. Although only one detector 140 is depicted in FIG. 1, in some embodiments, sensor 102 may include additional detectors located at different distances from the light source 130.

Sensor 102 may also include additional components not depicted in FIG. 1. For example, sensor 102 may include an internal power source (e.g., a battery) and a wireless transmitter for communicating with monitor 104. As another example, sensor 102 may include additional sensor components such as, for example, a temperature sensor.

In the embodiment shown, monitor 104 includes control circuit 110, light drive circuit 120, front end processing circuit 150, back end processing circuit 170, user interface 180, and communication interface 190. Monitor 104 may be communicatively coupled to sensor 102 via wired communication, wireless communication, or both. Wired communication may use a cable that includes one or more electronic conductors, one or more optical fibers, any other suitable communication components, any suitable insulation or sheathing, or any combination thereof. Monitor 104 may include a sensor port for mating with the cable.

Control circuit 110 may be coupled to light drive circuit 120, front end processing circuit 150, and back end processing circuit 170, and may be configured to control the operation of these components. In some embodiments, control circuit 110 may be configured to provide timing control signals to coordinate their operation. For example, light drive circuit 120 may generate a light drive signal, which may be used to turn on and off light source 130, based on the timing control signals. The front end processing circuit 150 may use the timing control signals to operate synchronously with light drive circuit 120. For example, front end processing circuit 150 may synchronize the operation of an analog-to-digital converter and a demultiplexer with the light drive signal based on the timing control signals. In addition, the back end processing circuit 170 may use the timing control signals to coordinate its operation with front end processing circuit 150.

Light drive circuit 120, as discussed above, may be configured to generate a light drive signal that is provided to light source 130 of sensor 102. The light drive signal may, for example, control the intensity of light source 130 and the timing of when light source 130 is turned on and off. In some embodiments, light drive circuit 120 may comprise a power supply and a switch for selectively applying power to light source 130. When light source 130 is configured to emit two or more wavelengths of light, the light drive signal may be configured to control the operation of each wavelength of light. The light drive signal may comprise a single signal or may comprise multiple signals (e.g., one signal for each wavelength of light). An illustrative light drive signal is shown in FIG. 2A.

Figure 2A:
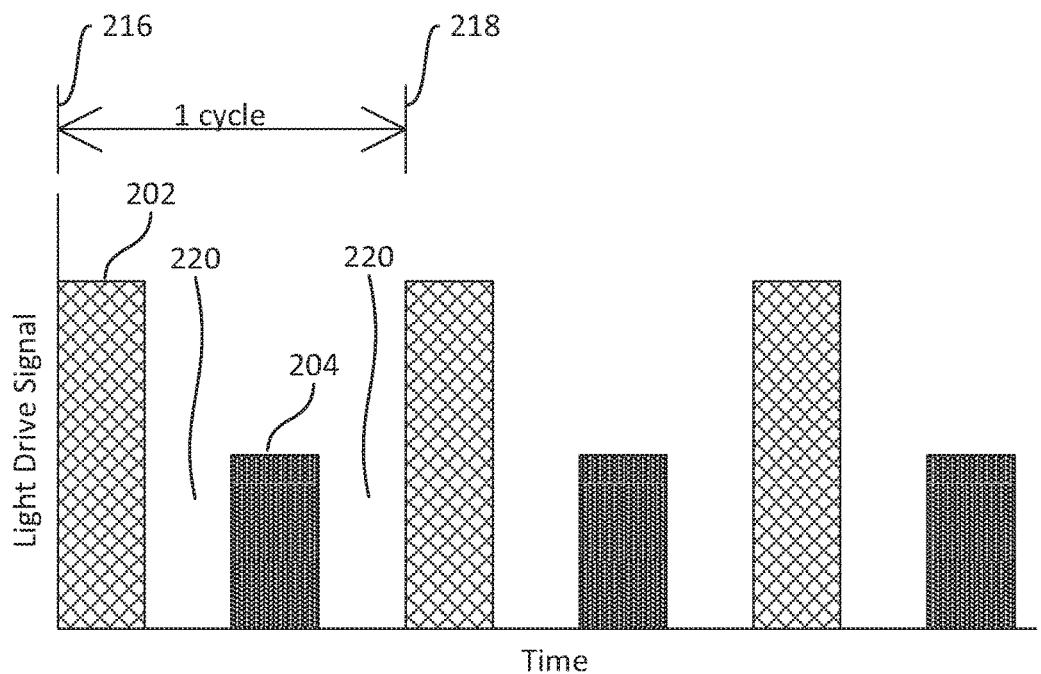
FIG. 2A shows an illustrative plot of a light drive signal in accordance with some embodiments of the present disclosure.

FIG. 2A shows an illustrative plot of a light drive signal including red light drive pulse 202 and IR light drive pulse 204 in accordance with some embodiments of the present disclosure. Light drive pulses 202 and 204 are illustrated as square waves. These pulses may include shaped waveforms rather than a square wave. Light drive pulses 202 and 204 may be generated, for example, by light drive circuit 120 under the control of control circuit 110. As used herein, drive pulses may refer to the high and low states of a shaped pulse, switching power or other components on and off, high and low output states, high and low values within a continuous modulation, other suitable relatively distinct states, or any combination thereof. The light drive signal may be provided to light source 130 to drive red and IR light emitters within light source 130. Light drive pulses 202 and 204 may have similar or different amplitudes. The amplitudes can be individually controlled by light drive circuit 120.

When the red and IR light sources are driven in this manner they emit pulses of light at their respective wavelengths into the tissue of a subject in order to generate sensor signals that include physiological information that physiological monitoring system 100 may process to calculate physiological parameters. It will be understood that the light drive amplitudes of FIG. 2A are merely exemplary and that any suitable amplitudes or combination of amplitudes may be used, and may be based on the light sources, the subject tissue, the determined physiological parameter, modulation techniques, power sources, any other suitable criteria, or any combination thereof.

The light drive signal of FIG. 2A may also include "off" periods 220 between the red and IR light drive pulses. "Off" periods 220 are periods during which no drive current may be applied to light source 130. "Off" periods 220 may be provided, for example, to prevent overlap of the emitted light, since light source 130 may require time to turn completely on and completely off. "Off" periods may also be referred to as dark periods, in that the emitters are dark or returning to dark during that period. The period from time 216 to time 218 may be referred to as a drive cycle. After time 218, the drive cycle may be repeated (e.g., as long as a light drive signal is provided to light source 130). It will be understood that the starting point of the drive cycle is merely illustrative and that the drive cycle can start at any location within FIG. 2A. It will be understood that the particular square pulses illustrated in FIG. 2A are merely exemplary and that any suitable light drive scheme is possible. For example, light drive schemes may include shaped pulses, sinusoidal modulations, time division multiplexing other than as shown, frequency division multiplexing, phase division multiplexing, any other suitable light drive scheme, or any combination thereof.

Referring back to FIG. 1, front end processing circuit 150 may receive a detection signal from detector 140 and provide one or more processed signals to back end processing circuit 170. The term "detection signal," as used herein, may refer to any of the signals generated within front end processing circuit 150 as it processes the output signal of detector 140. Front end processing circuit 150 may perform various analog and digital processing of the detector signal. One suitable detector signal that may be received by front end processing circuit 150 is shown in FIG. 2B.

Figure 2B:
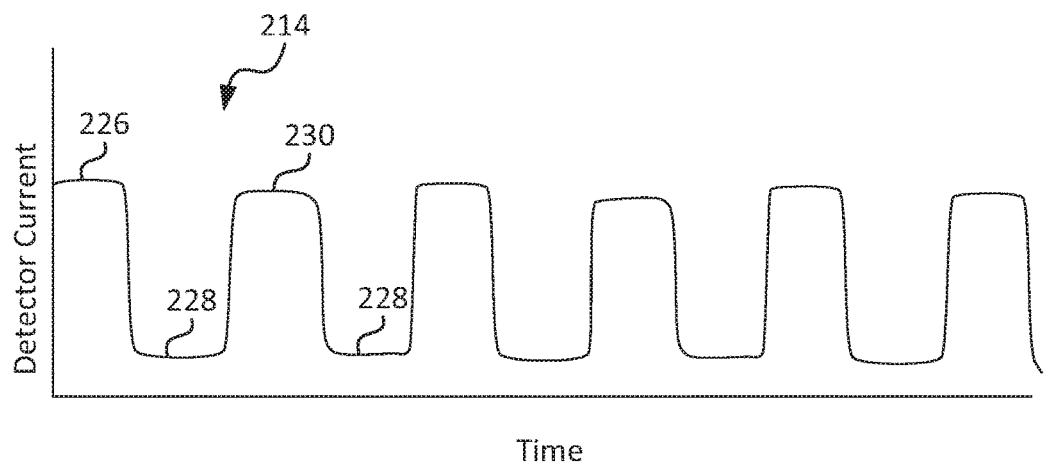
FIG. 2B shows an illustrative plot of a detector signal that may be generated by a sensor in accordance with some embodiments of the present disclosure.

FIG. 2B shows an illustrative plot of detector current waveform 214 that may be generated by a sensor in accordance with some embodiments of the present disclosure. The peaks of detector current waveform 214 may represent current signals provided by a detector, such as detector 140 of FIG. 1, when light is being emitted from a light source. The amplitude of detector current waveform 214 may be proportional to the light incident upon the detector. The peaks of detector current waveform 214 may be synchronous with drive pulses driving one or more emitters of a light source, such as light source 130 of FIG. 1. For example, detector current peak 226 may be generated in response to a light source being driven by red light drive pulse 202 of FIG. 2A, and peak 230 may be generated in response to a light source being driven by IR light drive pulse 204. Valleys 228 of detector current waveform 214 may be synchronous with periods of time during which no light is being emitted by the light source, or the light source is returning to dark, such as "off" periods 220. While no light is being emitted by a light source during the valleys, detector current waveform 214 may not fall all of the way to zero.

It will be understood that detector current waveform 214 as depicted may be an at least partially idealized representation of a detector signal, assuming near perfect light signal generation, transmission, and detection. It will be understood that an actual detector current will include amplitude fluctuations, frequency deviations, droop, overshoot, undershoot, rise time deviations, fall time deviations, other deviations from the ideal, or any combination thereof.

Referring back to FIG. 1, front end processing circuit 150, which may receive a one or more detection signals, such as detector current waveform 214, may include analog conditioning 152, analog-to-digital converter (ADC) 154, demultiplexer 156, digital conditioning 158, decimator/interpolator 160, and ambient subtractor 162.

Analog conditioning 152 may perform any suitable analog conditioning of the detector signal. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. In some embodiments, one or more gain settings may be used in analog conditioning 152 to adjust the amplification of the detector signal.

The conditioned analog signal may be processed by analog-to-digital converter 154, which may convert the conditioned analog signal into a digital signal. Analog-to-digital converter 154 may operate under the control of control circuit 110. Analog-to-digital converter 154 may use timing control signals from control circuit 110 to determine when to sample the analog signal. Analog-to-digital converter 154 may be any suitable type of analog-to-digital converter of sufficient resolution to enable a physiological monitor to accurately determine physiological parameters.

Demultiplexer 156 may operate on the analog or digital form of the detector signal to separate out different components of the signal. For example, detector current waveform 214 of FIG. 2B includes a red component corresponding to peak 226, an IR component corresponding to peak 230, and at least one ambient component corresponding to valleys 228. Demultiplexer 156 may operate on detector current waveform 214 of FIG. 2B to generate a red signal, an IR signal, a first ambient signal (e.g., corresponding to the ambient component corresponding to valley 228 that occurs immediately after the peak 226), and a second ambient signal (e.g., corresponding to the ambient component corresponding to valley 228 that occurs immediately after peak 230). Demultiplexer 156 may operate under the control of control circuit 110. For example, demultiplexer 156 may use timing control signals from control circuit 110 to identify and separate out the different components of the detector signal.

Digital conditioning 158 may perform any suitable digital conditioning of the detector signal. Digital conditioning 158 may include any type of digital filtering of the signal (e.g., low pass, high pass, band pass, notch, or any other suitable filtering), amplifying, performing an operation on the signal, performing any other suitable digital conditioning, or any combination thereof.

Decimator/interpolator 160 may decrease the number of samples in the digital detector signal. For example, decimator/interpolator 160 may decrease the number of samples by removing samples from the detector signal or replacing samples with a smaller number of samples. The decimation or interpolation operation may include or be followed by filtering to smooth the output signal.

Ambient subtractor 162 may operate on the digital signal. In some embodiments, ambient subtractor 162 may remove dark or ambient contributions to the received signal or signals.

The front end processing circuit 150 may be configured to take advantage of the full dynamic range of analog-to-digital converter 154. This may be achieved by applying one or more gains to the detection signal, by analog conditioning 152 to map the expected range of the signal to the full or close to full output range of analog-to-digital converter 154.

The components of front end processing circuit 150 are merely illustrative and any suitable components and combinations of components may be used to perform the front end processing operations.

Back end processing circuit 170 may include processor 172 and memory 174. Processor 172 may be adapted to execute software, which may include an operating system and one or more applications, as part of performing the functions described herein. Processor 172 may receive and further process sensor signals received from front end processing circuit 150. For example, processor 172 may determine one or more physiological parameters based on the received physiological signals. Processor 172 may include an assembly of analog or digital electronic components. Processor 172 may calculate physiological information. For example, processor 172 may compute one or more of fluid responsiveness, a blood oxygen saturation (e.g., arterial, venous, regional, or a combination thereof), pulse rate, respiration rate, respiration effort, blood pressure, hemoglobin concentration (e.g., oxygenated, deoxygenated, and/or total), any other suitable physiological parameters, or any combination thereof. Processor 172 may perform any suitable signal processing of a signal, such as any suitable scaling, band-pass filtering, adaptive filtering, closed-loop filtering, any other suitable filtering, and/or any combination thereof. Processor 172 may also receive input signals from additional sources not shown. For example, processor 172 may receive an input signal containing information about treatments provided to the subject from user interface 180. Additional input signals may be used by processor 172 in any of the calculations or operations it performs in accordance with back end processing circuit 170 or monitor 104.

Memory 174 may include any suitable non-transitory computer-readable media capable of storing information that can be interpreted by processor 172. In some embodiments, memory 174 may store calculated values, such as fluid responsiveness parameters, pulse rate, blood pressure, blood oxygen saturation, fiducial point locations or characteristics, initialization parameters, cardiac output, adaptive filter parameters, recommended amount of fluid to be administered, any other calculated values, or any combination thereof, in a memory device for later retrieval. In some embodiments, memory 174 may store information regarding fluid responsiveness thresholds, blood oxygen saturation thresholds, regions of the subject being analyzed, amounts of fluid administered, and any combination thereof in a memory device for later retrieval. This information may be data or may take the form of computer-executable instructions, such as software applications, that cause a processor to perform certain functions and/or computer-implemented methods. Computer storage media may include volatile and non-volatile, removable and non-removable media implemented in any method or technology for storage of information such as computer-readable instructions, data structures, program modules, or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. Back end processing circuit 170 may be communicatively coupled with user interface 180 and communication interface 190.

User interface 180 may include user input 182, display 184, and speaker 186. User interface 180 may include, for example, any suitable device such as one or more medical devices (e.g., a medical monitor that displays various physiological parameters, a medical alarm, or any other suitable medical device that either displays physiological parameters or uses the output of back end processing 170 as an input), one or more display devices (e.g., monitor, personal digital assistant (PDA), mobile phone, tablet computer, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

User input 182 may include any type of user input device such as a keyboard, a mouse, a touch screen, buttons, switches, a microphone, a joy stick, a touch pad, or any other suitable input device. The inputs received by user input 182 can include information about the subject, such as age, weight, height, diagnosis, medications, treatments including fluid administered thereto, and so forth.

In an embodiment, the subject may be a medical patient and display 184 may exhibit a list of values which may generally apply to the patient, such as, for example, age ranges or medication families, which the user may select using user input 182. Additionally, display 184 may display, for example, an estimate of a subject's fluid responsiveness information, blood oxygen saturation, pulse rate information, respiration rate and/or effort information, blood pressure information, hemoglobin concentration information, cardiac output, any other parameters, and any combination thereof. Display 184 may also display an indication of treatment to be given to the subject, including, for example, an indication of whether or not to administer fluid, how much fluid to administer, an indication of the effectiveness of the treatment, any other information regarding fluid administration, and any combination thereof. Display 184 may include any type of display such as a cathode ray tube display, a flat panel display such as a liquid crystal display or plasma display, or any other suitable display device. Speaker 186 within user interface 180 may provide an audible sound that may be used in various embodiments, such as for example, sounding an audible alarm in the event that a patient's physiological parameters are not within a predefined normal range, or sounding an alarm in the event that the patient's fluid administration should be started or stopped.

Communication interface 190 may enable monitor 104 to exchange information with external devices. Communication interface 190 may include any suitable hardware or hardware and software, which may allow monitor 104 to communicate with electronic circuitry, a device, a network, a server or other workstations, a display, or any combination thereof. In some embodiments, communications interface 190 is coupled to a sensor input port or a digital communications port of an external device. Communication interface 190 may include one or more receivers, transmitters, transceivers, antennas, plug-in connectors, ports, communications buses, communications protocols, device identification protocols, any other suitable hardware and software, or any combination thereof. Communication interface 190 may be configured to allow wired communication, wireless communication, or both. In some embodiments, communications interface 190 may enable monitor 104 to exchange information with external devices such as a regional oximeter, a pulse oximeter, any other suitable external devices, and any combination thereof. For example, communications interface 190 may receive oxygen saturation and/or fluid responsiveness information from any of the foregoing external devices, any other suitable devices, or any suitable combination thereof. In some embodiments, communications interface 190 may enable monitor 104 to control external devices configured to automatically administer fluid to a subject. For example, communications interface 190 may receive a signal indicative of fluid administration to be provided to the subject from processing equipment and may send this signal to a fluid administration mechanism to carry out the fluid administration. In some embodiments, communications interface 190 may enable monitor 104 to exchange information with a multi-parameter monitor or a calibration device. The calibration device may be powered by monitor 104, a battery, or by a conventional power source such as a wall outlet. In some embodiments, the calibration device is completely integrated within monitor 104. In some embodiments, the calibration device may include a manual input device used by a user to manually input reference signal measurements obtained from some other source (e.g., an external invasive or non-invasive physiological measurement system).

It will be understood that the components of physiological monitoring system 100 that are shown and described as separate components are shown and described as such for illustrative purposes only. In some embodiments the functionality of some of the components may be combined in a single component. For example, the functionality of front end processing circuit 150 and back end processing circuit 170 may be combined in a single processor system. Additionally, in some embodiments the functionality of some of the components of monitor 104 shown and described herein may be divided over multiple components. For example, some or all of the functionality of control circuit 110 may be performed in front end processing circuit 150, in back end processing circuit 170, or both. In other embodiments, the functionality of one or more of the components may be performed in a different order or may not be required. In an embodiment, all of the components of physiological monitoring system 100 can be realized in processor circuitry. In some embodiments, any of the components of FIG. 1 may be referred to collectively as processing equipment. It will understood that, as used herein, the term "circuit" refers to structure such as, for example, an electronic circuit, a portion of an electronic circuit, or a combination of electronic circuits.

Figure 3:
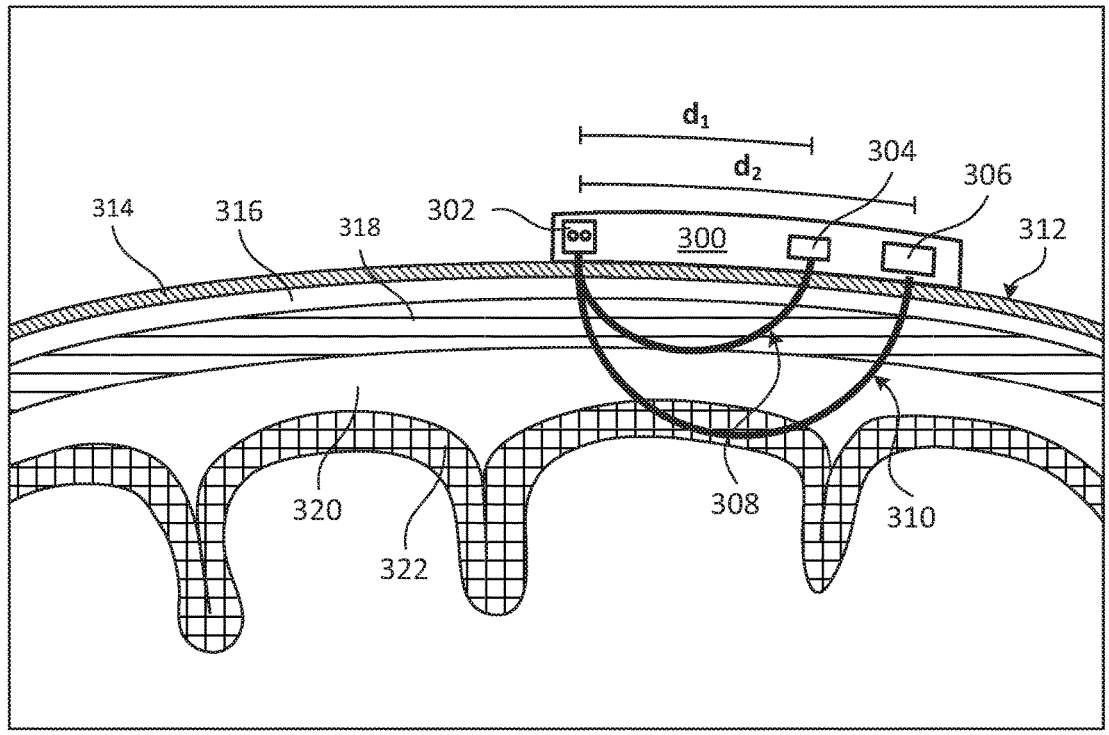
FIG. 3 is a cross-sectional view of an illustrative regional oximeter sensor unit applied to a subject's tissue in accordance with some embodiments of the present disclosure.

FIG. 3 is a cross-sectional view of an illustrative regional oximeter sensor unit 300 applied to a subject's cranium in accordance with some embodiments of the present disclosure. Regional oximeter sensor unit 300 includes light source 302, near detector 304, and far detector 306 and is shown as positioned on a subject's forehead 312. In the illustrated embodiment, light source 302 generates a light signal, which is shown traveling first and second mean path lengths 308 and 310, which traverse the subject's cranial structure at different depths. The subject's cranial structure includes outer skin 314, shallow tissue 316, and cranial bone 318 (i.e., the frontal shell of the skull). Beneath cranial bone 318 is Dura Mater 320 and cerebral tissue 322.

In some embodiments, light source 302 of sensor unit 300 may include one or more emitters for emitting light into the tissue of a subject to generate physiological signals. Detectors 304 and 306 may be positioned on sensor unit 300 such that near detector 304 is located at a distance $d_1$ from light source 302 and far detector 306 is located at a distance $d_2$ from light source 302. As shown, distance $d_1$ is shorter than distance $d_2$, and it will be understood that any suitable distances $d_1$ and $d_2$ may be used such that mean path length 308 of light detected by near detector 304 is shorter than the mean path length 310 of far detector 306. Near detector 304 may receive the light signal after it has traveled first mean path length 308, and far detector 306 may receive the light signal after it has traveled second mean path length 310. First mean path length 308 may traverse the subject's outer skin 314, shallow tissue 316, cranial bone 318, and Dura Mater 320. In some embodiments, first mean path length 308 may also traverse shallow cerebral tissue 322. Second mean path length 310 may traverse the subject's outer skin 314, shallow tissue 316, cranial bone 318, Dura Mater 320, and cerebral tissue 322.

In some embodiments, regional oximeter sensor unit 300 may be part of a regional oximetry system for determining the amount of light absorbed by a region of a subject's tissue. In some embodiments, regional oximeter sensor unit 300 may be incorporated into physiological monitoring system 100 as described above with respect to FIG. 1. For example, regional oximeter sensor unit 300 may be incorporated into or replace one or more sensors 102 of physiological monitoring system 100 as described above with respect to FIG. 1. As described in detail above, for each wavelength of light, an absorption value may be determined based on the light signal on first mean path length 308 received at near detector 304, and an absorption value may be determined based on the light signal on second mean path length 310 received at far detector 306. For each wavelength of light, a differential absorption value may be computed based on the difference between the absorption values determined for near detector 304 and far detector 306. The differential absorption values may be representative of the amount of light absorbed by cerebral tissue 322 at each wavelength. In some embodiments, the differential absorption values $\Delta A_{\lambda,i,j}$ may be given by:

$$\Delta A_{\lambda,i,j} = A_{\lambda,i} - A_{\lambda,j}, \quad (1)$$

where $A_{\lambda,i}$ denotes the attenuation of light between light source 302 and far detector 306, $A_{\lambda,j}$ denotes the attenuation of light between light source 302 and near detector 304, and the λ denotes a wavelength of light. In some embodiments, a detected light signal may be normalized based on the amount of light emitted by light source 302 and the amount of light detected at the respective detector (i.e., near detector 304 or far detector 306). The processing equipment may determine the differential absorption values $\Delta A_{\lambda,i,j}$ based on eq. 1, using normalized values for the attenuation of light between light source 302 and far detector 306 and the attenuation of light between light source 302 and near detector 304. Once the differential absorption values $\Delta A_{\lambda,i,j}$ are determined, the regional blood oxygen saturation can be determined or estimated using any suitable technique for relating the regional blood oxygen saturation to the differential absorption values $\Delta A_{\lambda,i,j}$. Although described above in terms of oxygen saturation of cerebral or other brain-related tissue, it will be understood that similar techniques may be used to determine regional oxygen saturation in any suitable tissue or portion thereof. For example, similar techniques may be used to determine oxygen saturation of a subject's kidney, abdomen, any components or sub-regions thereof, and/or any other suitable regions.

As described above, respiratory variation in the arterial blood pressure waveform is known to be a good predictor of a subject's fluid responsiveness. In particular, the PPV of a subject is known to be a good predictor of fluid responsiveness, but, as described above, requires invasive procedures to determine. Accordingly, determining respiratory variation in a PPG signal from a pulse oximeter may provide a non-invasive alternative to determining the PPV of a subject. Determination of fluid responsiveness in accordance with the present disclosure will be discussed with reference to FIG. 4 below. Although a PPG signal from a pulse oximeter is used to illustrate embodiments of the present disclosure, it will be understood that the techniques described herein are not limited to PPG signals and pulse oximeters and may be applied to any suitable physiological signals and monitoring devices, including, for example, signals received from regional oximeters as described above with respect to FIG. 3.

Figure 4:
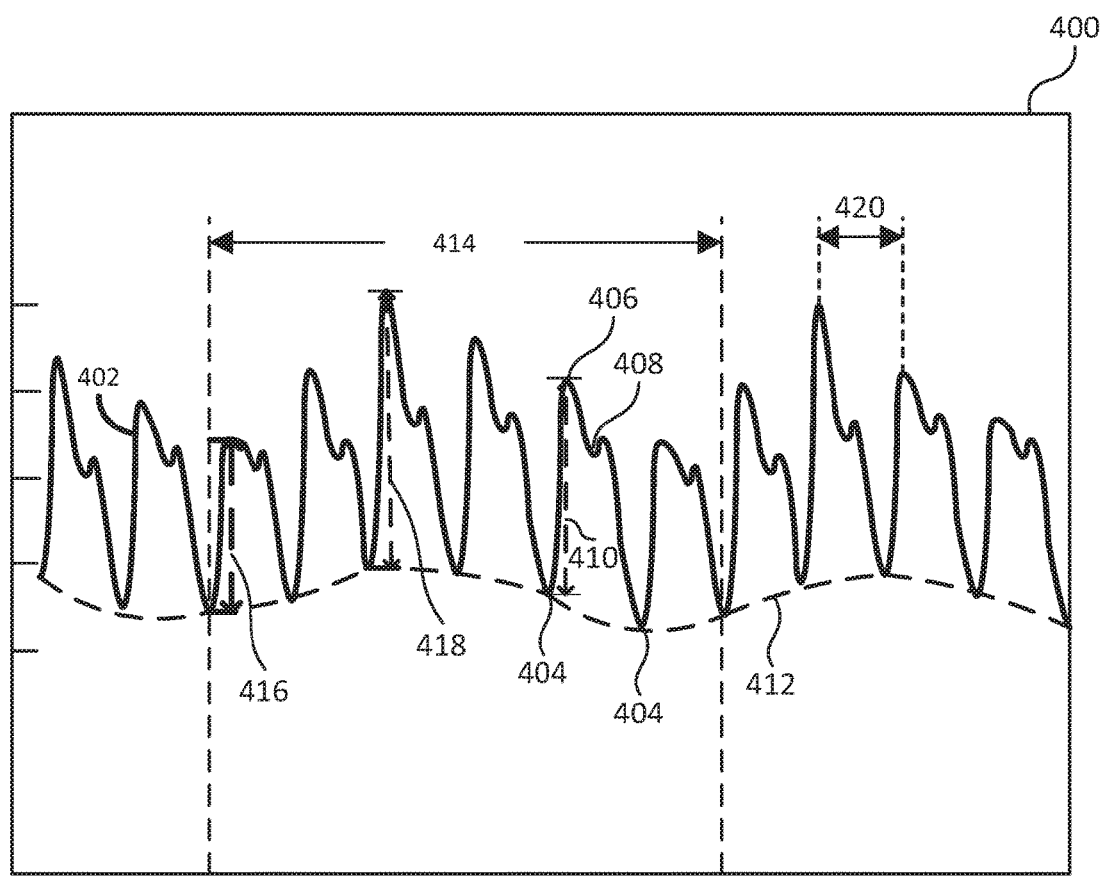
FIG. 4 shows an illustrative plot of a PPG waveform reflecting respiratory modulations in accordance with some embodiments of the present disclosure.

FIG. 4 shows an illustrative plot 400 of PPG waveform 402 reflecting respiratory modulations in accordance with some embodiments of the present disclosure. PPG waveform 402 may be generated, for example, by system 100 of FIG. 1. As illustrated, PPG waveform 402 represents the absorption of light by a subject's tissue over time. PPG waveform 402 includes pulses where the absorption of light increases due to the increased volume of blood in the arterial blood vessel due to cardiac pulses. In some embodiments, pulses may be identified between adjacent valleys 404 and as illustrated may include a peak 406 and a dicrotic notch 408. The pulses include an upstroke between the first valley and the main peak. For example, an upstroke is depicted in FIG. 4 between the first valley 404 and peak 406. The amplitude of this upstroke is depicted as amplitude 410 measured from the first valley 404 to peak 406. Other amplitude values may be derived from the PPG waveform, such as a downstroke amplitude, average amplitude, or area under the pulse. In some embodiments, the amplitude of a pulse may be determined by subtracting a minimum value of PPG waveform 402 from a maximum value of PPG waveform 402 within a segment of PPG waveform 402 that generally corresponds to the period of a pulse. PPG waveform 402 also includes a varying baseline 412. PPG waveform 402 modulates above baseline 412 due to the pulses.

For most subjects, the PPG signal is affected by the subject's respiration, i.e. inhaling and exhaling, resulting in certain respiration modulations in the PPG waveform. FIG. 4 illustrates respiration modulations in PPG waveform 402 as a result of the subject's inhaling and exhaling. One type of respiratory modulation is the modulation of baseline 412 of PPG waveform 402. The effect of the subject's breathing in and out causes the baseline of the waveform 402 to move up and down, cyclically, with the subject's respiration. The baseline may be tracked by following any fiducial of PPG waveform 402, such as the peaks 406, valleys 404, dicrotic notches 408, median value, or any other fiducials. A second type of respiration-induced modulation of PPG waveform 402 is the modulation of pulse amplitudes. As the patient breathes in and out, the amplitude of the pulses decrease and increase, with larger amplitudes tending to coincide with the top of the baseline shift, and smaller amplitudes tending to coincide with the bottom of the baseline shift (though the larger and smaller amplitudes do not necessarily fall at the top and bottom of the baseline shift). A third respiratory type of modulation is the modulation of period 420 between pulses (also referred to as frequency modulation). Each of these modulations may be referred to as a respiratory component of PPG waveform 402, or a respiratory-induced modulation of PPG waveform 402. It should be noted that a particular individual may exhibit only the baseline modulation, or only the amplitude modulation, or only the frequency modulation, or any combination thereof. As referred to herein, a respiratory component of the PPG waveform 402 includes any one of these respiratory-induced modulations of PPG waveform 402, a measure of these modulations, or a combination of them.

The respiratory modulations of PPG waveform 402 can be affected by a subject's fluid status. For example, a hypovolemic subject may exhibit relatively larger respiratory variations of PPG waveform 402. When a subject loses fluid, the subject may have decreased cardiac output or stroke volume, which tends to increase the respiratory variations present in the subject's PPG waveform. Specifically, the baseline modulation, amplitude modulation, and frequency modulation may become more pronounced. Thus, larger respiratory modulations may indicate that the subject will respond favorably to fluid loading, whereas smaller respiratory modulations may indicate that a patient may not respond favorably to fluid loading. The respiratory modulations of PPG waveform 402 may be identified and used to determine a subject's fluid responsiveness.

In some embodiments, a physiological monitor receives a PPG signal and determines a parameter indicative of fluid responsiveness based on the PPG signal. In some embodiments, the parameter indicative of fluid responsiveness is a measure of a subject's likely response to fluid therapy. In some embodiments, the parameter indicative of fluid responsiveness is a metric that reflects a degree of respiratory variation of the PPG signal. One example of a parameter indicative of fluid responsiveness is a measure of the amplitude modulations of the PPG signal, such as Delta POP (DPOP or ΔPOP). Another example of a parameter indicative of fluid responsiveness is a measure of the baseline modulation of the PPG signal. In some embodiments, other suitable metrics or combinations of metrics may be used to assess the respiratory modulation of the PPG signal. For example, a parameter indicative of fluid responsiveness may be based on the amplitudes or areas of acceptable pulses within a particular time frame or window. For example, as illustrated in FIG. 4, minimum amplitude 416 of the pulses within respiratory period 414 may be subtracted from maximum amplitude 418 within respiratory period 414 and then divided by an average or mean value of minimum amplitude 416 and maximum amplitude 418. In some embodiments, a parameter indicative of fluid responsiveness may be derived from the period or frequency of pulses within a time frame or window. For example, a modulation or variation in the period or frequency among two or more cardiac pulses may be used to derive a parameter indicative of fluid responsiveness. In general, the parameter indicative of fluid responsiveness may be based on one or more respiratory variations exhibited by the PPG waveform 402. Further, a parameter indicative of fluid responsiveness may be determined through the use of wavelet transforms, such as described in United States Patent Application Publication No. 2010/0324827, entitled "Fluid Responsiveness Measure," which is hereby incorporated by reference in its entirety.

In some embodiments, DPOP is used as the parameter indicative of fluid responsiveness. In some embodiments, the DPOP metric can be calculated from PPG waveform 402 for a particular time window as follows:

$$DPOP=(AMP_{max}-AMP_{min})/AMP_{ave}, \quad (2)$$

where $AMP_{max}$ represents the maximum amplitude (such as maximum amplitude 418 in FIG. 4) during a time window (such as respiratory period 414 in FIG. 4), $AMP_{min}$ represents the minimum amplitude (such as minimum amplitude 416 in FIG. 4) during the time window, and $AMP_{ave}$ is the average of the two, as follows:

$$AMP_{ave}=(AMP_{max}+AMP_{min})/2 \quad (3)$$

In some embodiments, $AMP_{max}$ and $AMP_{min}$ may be measured at other locations of the PPG, such as within or along a pulse. DPOP is a measure of the respiratory variation in the AC portion of the PPG signal. DPOP is a unit-less value, and in some embodiments can be expressed as a percentage. In some embodiments, a scaling factor may be applied to DPOP so that DPOP more closely corresponds to PPV. For example, the scaling factor can be applied to the terms in the numerator or denominator of equation 2, or to the computed DPOP value. In some embodiments, respiratory period 414 is one respiratory cycle (inhalation and exhalation). In some embodiments, respiratory period 414 is a fixed duration of time that approximates one respiratory cycle, such as 5 seconds, 10 seconds, or any other suitable duration. In some embodiments, respiratory period 414 may be adjusted dynamically based on the subject's calculated or measured respiration rate, so that the period is approximately the same as one respiratory cycle period. In some embodiments, a signal turning point detector may be used to identify the maximum and minimum points in the PPG signal, in order to calculate the upstroke amplitudes. In some embodiments, $AMP_{ave}$ may be a filtered version of the PPG, such as a low-pass version of the PPG signal.

In some embodiments, it is desirable to determine the parameter indicative of fluid responsiveness by averaging the parameter as calculated in accordance with any of the embodiments described above over a second time window. For example, if DPOP is used as the parameter indicative of fluid responsiveness, and is calculated over a fixed duration of 10 seconds, it may be desirable to average the plurality of DPOP calculations performed over a fixed window of 120 seconds, effectively taking the average of 12 DPOP calculations to yield a parameter indicative of the subject's fluid responsiveness.

As described above, monitoring regional tissue oxygen saturation using NIRS can be useful in critically ill patients. Accordingly, it may be desirable to administer fluid to a subject based on both a parameter indicative of fluid responsiveness such as DPOP and a regional oxygen saturation parameter. Determination of fluid administration for a subject in accordance with the present disclosure will be discussed with reference to FIGS. 5-7 below.

Figure 5:
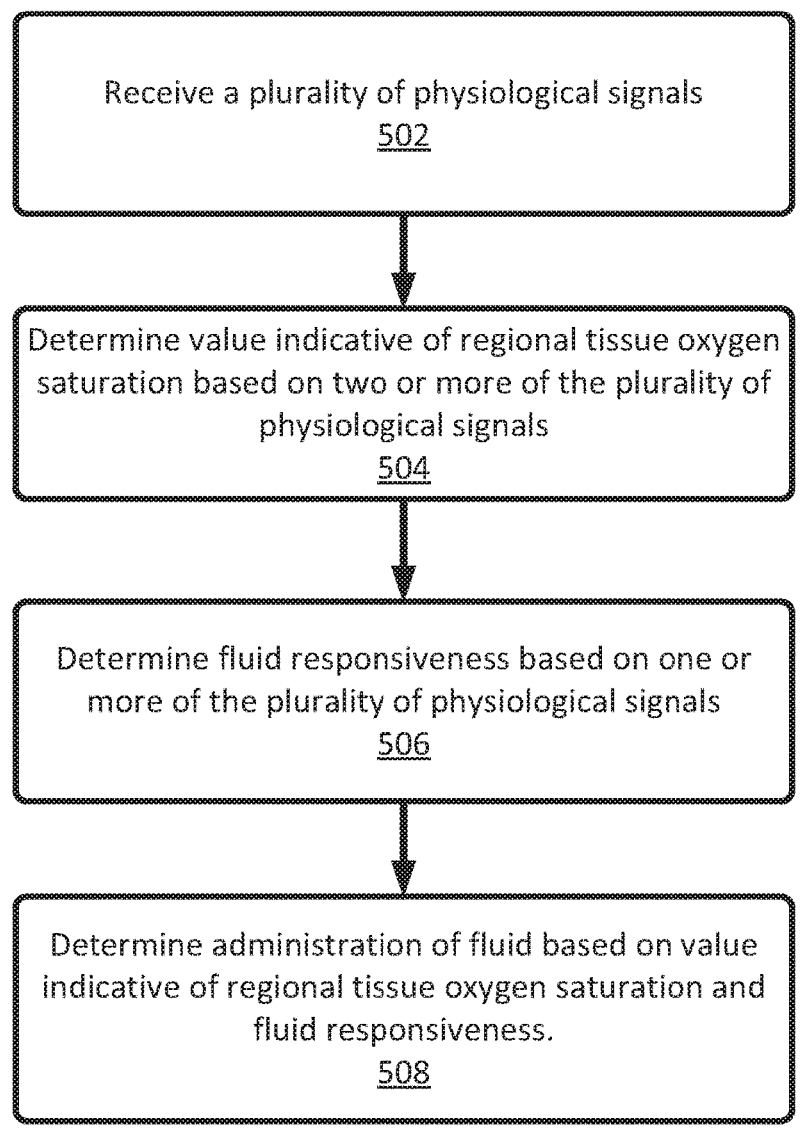
FIG. 5 shows an illustrative flow diagram for determining fluid administration in accordance with some embodiments of the present disclosure.
Figure 6:
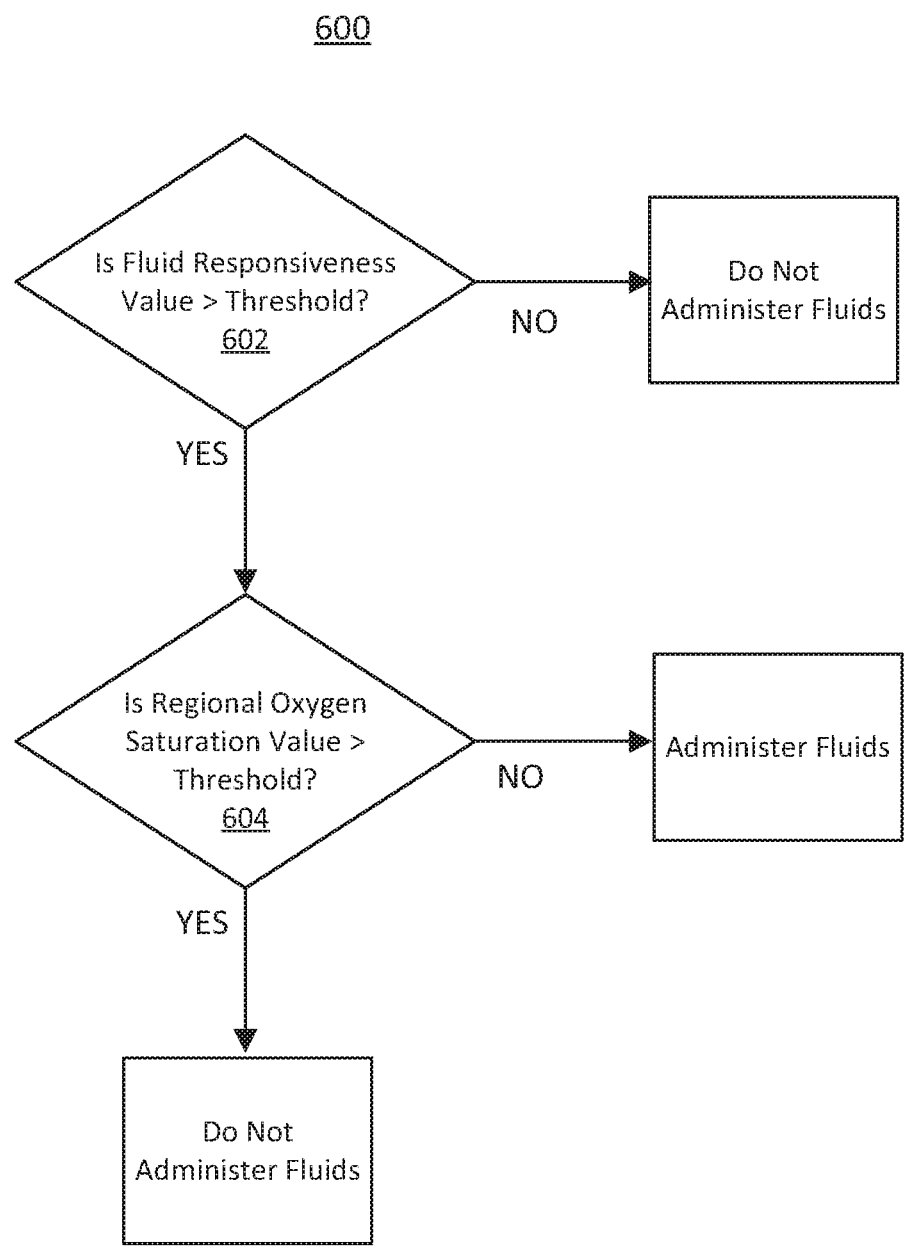
FIG. 6 shows an illustrative flow diagram for determining fluid administration in accordance with some embodiments of the present disclosure.

FIGS. 5 and 6 show illustrative flow diagrams 500 and 600 for determining fluid administration in accordance with some embodiments of the present disclosure. Although exemplary steps are described therein, it will be understood that steps may be omitted and that any suitable additional steps may be added for determining fluid administration. Although the steps described herein may be performed by any suitable device or system, in an exemplary embodiment, the steps may be performed by monitoring system 100 of FIG. 1, processing equipment thereof, any components and modules thereof, and any combination thereof.

Referring to FIG. 5, at step 502, the processing equipment may receive a plurality of physiological signals. The physiological signals may be indicative of light attenuated by a subject. For example, the physiological signals may include a PPG signal received from a pulse oximeter, a plurality of NIRS-derived signals received from a regional oximeter, or any suitable combination thereof. In some embodiments the physiological signal may include a PPV signal or a physiological signal indicative of a subject's PPV. In some embodiments, the physiological signals may be received from one or more sensors of the physiological monitoring system, from external sensors, from other suitable sources internal or external of the physiological monitoring system, or from any suitable combination thereof. For example, processing equipment may receive a plurality of physiological signals from sensor 102 as described above with respect to FIG. 1 and/or from regional oximeter sensor unit 300 incorporated into monitoring system 100 as described above with respect to FIGS. 1 and 3.

At step 504, the processing equipment may determine a value indicative of regional tissue oxygen saturation of a subject based on at least two of the plurality of physiological signals received in step 502. In some embodiments, back end processing circuit 170 of FIG. 1 may determine a value indicative of regional tissue oxygen saturation of the subject based on differential absorption values determined from at least two of the plurality of physiological and using any suitable technique for relating the differential absorption values to regional blood oxygen saturation signals as described above with respect to FIG. 3. In some embodiments, the value indicative of regional tissue oxygen saturation of a subject may be indicative of oxygen saturation in a particularly critical region of the subject as it relates to evaluation of fluid administration. For example, the value indicative of regional tissue oxygen saturation of a subject may be indicative of oxygen saturation in a subject's brain, kidney, abdomen, any components or sub-regions thereof, or any other suitable region of the subject.

Alternatively, in some embodiments, processing equipment may receive a value indicative of regional tissue oxygen saturation from an external device. For example, processing equipment may receive a value indicative of regional tissue oxygen saturation from an external regional oximeter via a communication interface.

At step 506 the processing equipment may determine a value indicative of fluid responsiveness based on one or more of the plurality of physiological signals received in step 502. The value indicative of fluid responsiveness may be determined in accordance with any of the above-described methods. In some embodiments, the value indicative of fluid responsiveness may be determined based on a PPG signal received from a pulse oximeter sensor. For example, the value indicative of fluid responsiveness may be determined based on a PPG signal indicative of IR light absorbed by a subject, a PPG signal indicative of red wavelength light absorbed by a subject, or any other suitable PPG signal. In some embodiments, the value indicative of fluid responsiveness may be determined based on at least one signal received from a regional oximeter sensor. For example, in some embodiments, the value indicative of fluid responsiveness may be determined based on at least one of the signals used in step 504 to determine the value indicative of regional tissue oxygen saturation. In some embodiments, the value indicative of fluid responsiveness may be determined based on respiratory variations identified in one or more of the plurality of physiological signals received in step 502. For example, the value indicative of fluid responsiveness may be determined by determining a plurality of amplitudes in a physiological signal and by identifying maximum and minimum amplitudes during a time window and dividing a difference between the amplitudes by an average of the amplitudes. For example the fluid responsiveness parameter may be determined based on equations (2)-(3) used to calculate DPOP as described above. In some embodiments, the value indicative of fluid responsiveness may be determined based on a perfusion index (PI) of one or more of the plurality of physiological signals received in step 502. For example, the PI may be calculated by determining the percent modulation of a physiological signal. In some embodiments, the percent modulation may be determined by determining the "AC" and "DC" components of a signal and taking a ratio of the AC and DC components. In some embodiments, a value indicative of fluid responsiveness may be determined by the following equation:

$$(PI_{max} - PI_{min})/PI_{ave}, \qquad (4)$$

where PI is the percent modulation of the signal, and $PI_{max}$, $PI_{min}$, and $PI_{ave}$ are any suitable maximum, minimum, and average values of PI over any suitable time window respectively.

At step 508 the processing equipment may determine the administration of fluid to a subject based on the value indicative of regional tissue oxygen saturation determined in step 504 and the value indicative of fluid responsiveness determined in step 506. In some embodiments, the processing equipment may determine whether to administer fluid to a subject based on the value indicative of regional tissue oxygen saturation received in step 504 and the value indicative of fluid responsiveness determined in step 506. For example, the processing equipment may determine to administer fluid to a subject only if the value indicative of regional tissue oxygen saturation is less than a suitable threshold and the value indicative of fluid responsiveness exceeds a suitable threshold. In some embodiments, the processing equipment may determine the amount of fluid to administer based on the value indicative of regional tissue oxygen saturation and the value indicative of fluid responsiveness. In some embodiments, the processing equipment may determine to reduce or increase the volume of fluid administered based on the values indicative of regional tissue oxygen saturation and fluid responsiveness. For example, if the value indicative of fluid responsiveness is above a certain threshold, e.g. 15%, the system may reduce the volume of fluid administered if the value indicative of regional tissue oxygen saturation is relatively high, and may increase the volume of fluid administered if the value indicative of regional tissue oxygen saturation is relatively low. In some embodiments, the processing equipment may use the value indicative of fluid responsiveness to guide therapy, and the value indicative of regional tissue oxygen saturation to determine when fluid administration has been optimized. For example, the processing equipment may continue to administer fluid as long as the value indicative of fluid responsiveness is above a certain threshold, e.g. 15%, until the value indicative of regional tissue oxygen saturation reaches a suitable threshold indicating adequate tissue perfusion. In some embodiments, step 508 may be performed in accordance with FIG. 6 as described below.

Although not shown in FIG. 5, additional steps may be performed whereby the processing equipment causes the fluid administration determined in step 508 to be provided to the subject. In some embodiments, processing equipment may cause a fluid administration mechanism coupled to the physiological monitoring system to administer fluid according to the determination in step 508. As will be understood by one of ordinary skill in the art, the fluid administration mechanism may be any suitable device for administering fluid to a subject. For example, processing equipment may cause an automated pump and syringe mechanism coupled to the system to start, stop, and/or modify the administration of fluid to the subject. In some embodiments, the processing equipment may generate control signals to cause the fluid administration mechanism to administer fluid in response to the determination in step 508. In some embodiments, processing equipment may provide an indication to an operator, via a display device coupled to the processing equipment, regarding the administration of fluid to be provided to the subject. For example, processing equipment may cause a display device to provide prompts for an operator. In some embodiments, processing equipment may cause a display device to prompt an operator to commence fluid administration, cease fluid administration, increase fluid administration, and/or decrease fluid administration. In some embodiments, processing equipment may cause a display device to prompt an operator regarding the specific amount of fluid to be administered to the subject.

FIG. 6 shows an illustrative flow diagram 600 for determining fluid administration in accordance with some embodiments of the present disclosure. At step 602, the processing equipment may compare a value indicative of fluid responsiveness to a threshold. In some embodiments, the fluid responsiveness threshold may be indicative of hypovolemia in the subject. For example, the fluid responsiveness threshold may be 15%. In some embodiments, the fluid responsiveness threshold may depend on physiological characteristics of the subject, physiological parameters of the subject, the presence of arrhythmias in the subject, the presence of drugs such as vasoactive drugs in the subject, settings of a ventilator being used by the subject, physical conditions such as the posture of the subject, any other suitable factors, and any combination thereof. In some embodiments, if the value indicative of fluid responsiveness is not greater than the fluid responsiveness threshold, the processing equipment may determine not to administer fluid to the subject. In some embodiments, if the value indicative of fluid responsiveness is not greater than the fluid responsiveness threshold, the processing equipment may determine to decrease the volume of fluid administered to the subject.

In some embodiments, if the value indicative of fluid responsiveness is greater than the fluid responsiveness threshold, the processing equipment may proceed to step 604.

At step 604, the processing equipment may compare a value indicative of regional oxygen saturation to a threshold. In some embodiments, the regional oxygen saturation threshold may be indicative of adequate end-tissue perfusion. In some embodiments, the regional oxygen saturation threshold may depend on the tissue or region evaluated, physiological characteristics of the subject, physiological parameters of the subject, any other suitable factors, and any combination thereof. In some embodiments, the value indicative of regional oxygen saturation may be used to "gate" the prescription of fluids. For example, the processing equipment may determine to start administering fluid to the subject only if the value indicative of regional oxygen saturation is not greater than the regional oxygen saturation threshold. In some embodiments, if the value indicative of regional oxygen saturation is greater than the regional oxygen saturation threshold, the processing equipment may determine not to administer fluid to the subject because the end-tissue perfusion is considered adequate.

In some embodiments, once it is determined in step 602 that the value indicative of fluid responsiveness is greater than the fluid responsiveness threshold, the processing equipment may determine or modify the amount of fluid to be administered to the subject based on the determination in step 604. For example, if the value indicative of regional oxygen saturation is relatively high, i.e., greater than the regional oxygen saturation threshold, then the processing equipment may determine that a relatively low fluid bolus (e.g., 250 ml) should be administered, and if the value indicative of regional oxygen saturation is not relatively high, i.e., less than or equal to the regional oxygen saturation threshold, then the processing equipment may determine that a standard fluid bolus (e.g., 500 ml) should be administered. In some embodiments, if fluid administration has already been initiated and the value indicative of regional oxygen saturation is not greater than the regional oxygen saturation threshold, then the processing equipment may determine to increase the volume of fluid administered to the subject. In some embodiments, if fluid administration has already been initiated and the value indicative of regional oxygen saturation is greater than the regional oxygen saturation threshold, then the processing equipment may determine to decrease the volume of fluid administered to the subject or stop the administration of fluid to the subject altogether.

Figure 7:
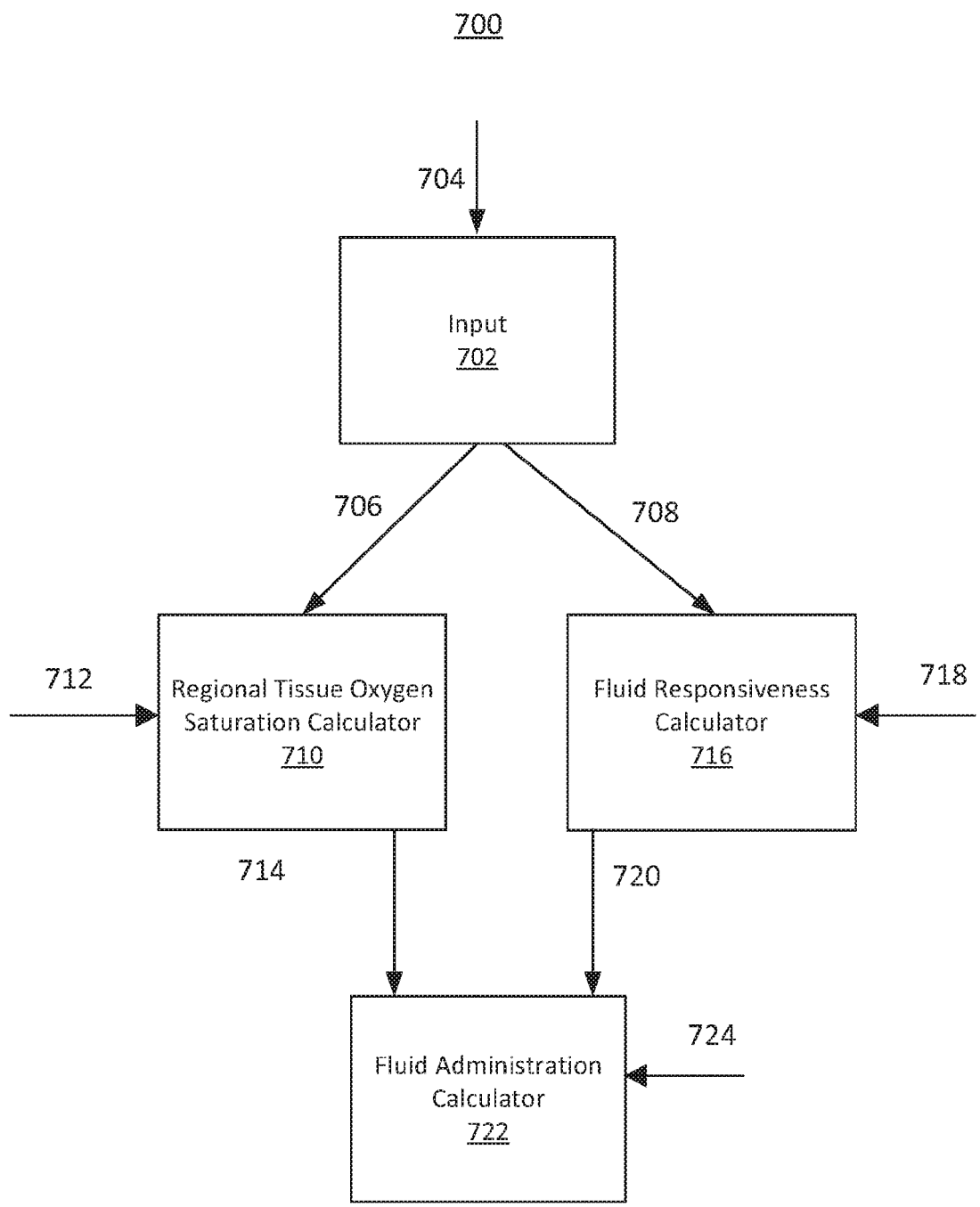
FIG. 7 shows an illustrative physiological monitor for determining fluid administration in accordance with some embodiments of the present disclosure.

FIG. 7 shows an illustrative physiological monitor 700 for determining fluid administration in accordance with some embodiments of the present disclosure. Monitor 700 includes input 702. In some embodiments, input 702 may include any suitable combination of components of monitor 100 for receiving a signal as described above with respect to FIG. 1. For example, input 702 may include sensor 102, light drive circuit 120, control circuit 110, and front end processing circuit 150 as described above with respect to FIG. 1, and may be configured to receive, generate and process signals as described above. In some embodiments, input 702 may include fewer components or additional components. Input 702 receives one or more physiological signals collectively referred to herein as signals 704. In some embodiments, signals 704 may be signals indicative of light absorbed by a subject and responsive to total oxygen saturation in a region of a subject's tissue. For example, the physiological signals 704 may be signals generated by a regional oximeter as described above with respect to FIGS. 1-3.

Input 702 generates outputs 706 and 708. Outputs 706 and 708 may include any or all of signals 704, components thereof, processed versions thereof, or any suitable combination thereof. In some embodiments, output 706 is passed to regional tissue oxygen saturation calculator 710. Regional tissue oxygen saturation calculator 710 is coupled to input 702 and may be configured to determine regional oxygen saturation in a region of a subject's tissue based on output 706 as described above with respect to FIG. 3 and step 504 of FIG. 5. For example, regional oxygen saturation may be determined by determining differential absorption values using values for the attenuation of light between a light source and two detectors, and using any suitable technique for relating the differential absorption values to regional blood oxygen saturation. In some embodiments, regional tissue oxygen saturation calculator 710 may include any suitable combination of components of monitor 100 as described above with respect to FIG. 1 for analyzing and processing physiological signals. For example, regional tissue oxygen saturation calculator 710 may include front end processing circuit 150, back end processing circuit 170, any components thereof, and/or any suitable combination thereof as described above with respect to FIG. 1, and may be configured to receive signals and process them as described above. In some embodiments, regional tissue oxygen saturation calculator 710 may include fewer components or additional components. Regional tissue oxygen saturation calculator 710 generates output 714 that is passed to fluid administration calculator 722. Output 714 may include the regional tissue oxygen saturation. In some embodiments, output 714 may also include information regarding the region or tissue being evaluated, a threshold associated with the regional tissue oxygen saturation that is indicative of adequate end-tissue perfusion, any suitable information regarding the regional tissue oxygen saturation value, and any suitable combination thereof.

In some embodiments, regional tissue oxygen saturation calculator 710 may be replaced by a regional tissue oxygen saturation input that receives a regional tissue oxygen saturation value 712 for a subject and passes the regional tissue oxygen saturation value 712 to fluid administration calculator 722. Regional tissue oxygen saturation input may include communication interface 190 of FIG. 1 configured to receive a regional tissue oxygen saturation value calculated by an external device.

In some embodiments, output 708 is passed to fluid responsiveness calculator 716. Fluid responsiveness calculator 716 is coupled to input 702 and may be configured to determine fluid responsiveness of a subject based on at least one of the physiological signals as described above with respect to FIG. 4 and step 506 of FIG. 5 and pass it to fluid administration calculator 722. For example, fluid responsiveness may be calculated by determining DPOP for one or more of the plurality of physiological signals using Eqs. 2-3 as described above, or by determining fluid responsiveness based on PI using Eq. 4 as described above. In some embodiments, fluid responsiveness calculator 716 may include any suitable combination of components of monitor 100 as described with respect to FIG. 1 for analyzing and processing a physiological signal. For example, fluid responsiveness calculator 716 may include front end processing circuit 150, back end processing circuit 170, any components thereof, and/or any suitable combination thereof as described above with respect to FIG. 1, and may be configured to receive signals and process them as described above. In some embodiments, fluid responsiveness calculator 716 may include fewer components or additional components. Fluid responsiveness calculator 716 generates output 720 that is passed to fluid administration calculator 722. Output 720 may include the fluid responsiveness value of a subject.

In some embodiments, fluid responsiveness calculator 716 may be replaced by a fluid responsiveness input that receives a fluid responsiveness value 718 for a subject and passes the fluid responsiveness value 718 to fluid administration calculator 722. The fluid responsiveness input may include communication interface 190 configured to receive a fluid responsiveness value calculated by an external device.

Fluid administration calculator 722 may determine a suitable fluid administration for a given subject and provide an indication thereof based on outputs 714 and 720. Fluid administration calculator 722 may include any suitable combination of components of monitor 100 as described with respect to FIG. 1 for processing the outputs from regional tissue oxygen saturation calculator 710 and fluid responsiveness calculator 716 and providing an indication regarding fluid administration. For example, fluid administration calculator 722 may include back end processing circuit 170, communication interface 190, any components thereof, and/or any suitable combination thereof as described above with respect to FIG. 1, and may be configured to receive fluid responsiveness values and regional oxygen saturation values, process them, determine the appropriate fluid administration for a given subject and provide indications regarding the fluid administration based thereon as described above. In some embodiments, fluid administration calculator 722 may include fewer components or additional components.

In addition to outputs 714 and 720 from regional tissue oxygen saturation calculator 710 and fluid responsiveness calculator 716 respectively, fluid administration calculator 722 may receive additional information 724. Additional information 724 may be received from an external device coupled to physiological monitoring system 700, from any sensors or detectors of physiological monitoring system 700, or from any memory associated therewith. Additional information 724 may include demographic information regarding the subject, other physiological parameters of the subject, information regarding the region or tissue being analyzed by regional tissue oxygen saturation calculator 710, information regarding suitable thresholds for regional oxygen saturation and/or fluid responsiveness, information regarding the amount and timing of fluid administered to the subject (including fluid actually administered), any other suitable information relevant to fluid administration, and any suitable combination thereof.

Fluid administration calculator 722 may process outputs 714 and 720 and additional information 724 and provide an indication regarding fluid administration in accordance with any of the techniques described above with respect to FIGS. 5-6. For example, fluid administration calculator 722 may compare the fluid responsiveness value to a threshold, compare the regional oxygen saturation value to a threshold, and determine whether to administer fluid and/or how much fluid to administer based on the comparisons. In some embodiments, fluid administration calculator may output an indication of this determination to be displayed on an external display to allow the caregiver to respond accordingly. For example, fluid administration calculator may output a signal to an external display that causes the display to prompt a caregiver when to start or stop fluid administration, and/or how much fluid to administer.

In some embodiments, fluid administration calculator 722 may be used for automated GDT of a subject. In some embodiments, fluid administration calculator 722 may output its fluid administration determination to a fluid administration mechanism configured to control the fluid administration of a subject, and may control the mechanism to adjust the fluid administration based on the monitored regional oxygen saturation and fluid responsiveness values. For example, fluid administration calculator 722 may output its fluid administration determination to a device including an automated pump coupled to a syringe used to administer fluid to a subject. In some embodiments, fluid administration calculator 722 may output a signal to cause such a device to start, stop, or otherwise modify the fluid administration. For example, if it is determined to stop or decrease fluid administration, fluid administration calculator 722 may cause the pump mechanism to stop or decrease pumping fluid, and if it is determined to start or increase fluid administration fluid administration calculator 722 may cause the pump mechanism to start or increase pumping fluid.

In some embodiments, fluid administration calculator 722 may also determine fluid administration based on the trend of both regional oxygen saturation and fluid responsiveness. In some embodiments, fluid administration calculator 722 may receive regional oxygen saturation and fluid responsiveness values in real time and determine fluid administration based on the trend of those values. For example, if fluid administration is initiated, and both regional oxygen saturation and fluid responsiveness values indicate improved hemodynamic status of the subject, fluid administration calculator 722 may determine that fluid administration should continue and may provide an alarm or other prompt to the caregiver as described above. If one or both of the regional oxygen saturation and fluid responsiveness values parameters are not indicating improved hemodynamic status, then fluid administration calculator 722 may determine that fluid administration should be stopped, and may provide an alarm or other prompt to the caregiver as described above. In some embodiments, the trend of both regional oxygen saturation and fluid responsiveness in response to fluid administered may be analyzed by fluid administration calculator 722 to determine the effectiveness of treatment and determine further fluid administration based thereon. As described above, fluid administration calculator 722 may, in some embodiments, receive information regarding the fluid administered to the subject. For example, fluid administration calculator 722 may receive an indication that fluid has been administered, an indication of when the fluid was administered and/or an indication of the volume of fluid that was administered. In some embodiments, fluid administration calculator 722 may evaluate any of the aforementioned information and the trend of the subsequent regional oxygen saturation and/or fluid responsiveness values received from regional tissue oxygen saturation calculator 710 and fluid responsiveness calculator 716, and determine whether the fluid administration is effective. For example, if fluid responsiveness decreases and regional oxygen saturation increases in response to fluid administration, thereby indicating an improved hemodynamic status in the subject, fluid administration calculator 722 may determine that fluid administration is effective and determine that fluid administration should be continued. In some embodiments, fluid administration calculator 722 may modify its fluid administration determination based thereon and output an indication of this determination to be displayed on an external display to allow the caregiver to respond accordingly. As another example, if both fluid responsiveness and regional oxygen saturation decrease in response to fluid administration, indicating worsened or unchanged hemodynamic status in the subject, fluid administration calculator 722 may determine that fluid administration is not effective, and may modify its fluid administration determination (e.g., determining to decrease or cease fluid administration) based thereon and output an indication of this determination to be displayed on an external display to allow the caregiver to respond accordingly. In some embodiments, if the trend of one of fluid responsiveness and regional oxygen saturation indicates improved hemodynamic status and the trend of the other is constant or inconclusive, fluid administration calculator 722 may determine or modify fluid administration depending on which parameter indicates improvement, the magnitude of the improvement, any other relevant factor, and any suitable combination thereof. For example, if fluid responsiveness remains constant but regional oxygen saturation indicates improved hemodynamic status, fluid administration calculator 722 may determine to continue fluid administration.

In some embodiments, the trend of regional oxygen saturation and fluid responsiveness values may be determined by any suitable method for analyzing the change in parameters over time. In some embodiments, current values of any of regional oxygen saturation and fluid responsiveness may be compared to respective starting values or values at particular times (e.g., corresponding to the initiation of fluid administration) to determine instantaneous trend values. In some embodiments, an average of instantaneous trend values over any suitable window may be computed and used to determine fluid administration and/or the effectiveness thereof as described above.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed:
1. A physiological monitoring system comprising:
  a pulse oximetry sensor configured to:
    detect at least one first wavelength of light from a first tissue of a subject; and
    generate a photoplethysmograph (PPG) signal based on the detected at least one first wavelength of light;
  a regional oxygen saturation sensor configured to detect at least one second wavelength of light from a second tissue of the subject and determine a value indicative of regional oxygen saturation in the second tissue; and
  a processor coupled to the pulse oximetry sensor and the regional oxygen saturation sensor, wherein the processor is configured to:
    receive the PPG signal;
    determine a value indicative of fluid responsiveness of the subject based on a change in the PPG signal over time;
    receive the value indicative of regional oxygen saturation in the second tissue; and determine whether to administer fluid to the subject based on the value indicative of regional oxygen saturation and the value indicative of fluid responsiveness.

2. The system of claim 1, wherein the value indicative of fluid responsiveness is determined based on respiratory variations identified in the PPG signal.

3. The system of claim 1, wherein the value indicative of fluid responsiveness is determined based on amplitude variations in the PPG signal.

4. The system of claim 1, wherein the value indicative of fluid responsiveness is determined based on variations of a percent modulation of the PPG signal.

5. The system of claim 1, wherein the value indicative of regional oxygen saturation is indicative of oxygen saturation in at least one of the subject's brain, kidney, and abdomen.

6. The system of claim 1 further comprising a fluid administration mechanism coupled to the processor configured to administer fluid to the subject based on the processor's determination of whether to administer fluid.

7. The system of claim 6, wherein the fluid administration mechanism comprises a syringe and an automated pump mechanism coupled to the syringe that actuates the syringe to administer fluid to the subject based on the processor's determination of whether to administer fluid.

8. The system of claim 1, wherein the processor is configured to determine whether to administer fluid to the subject by:
   comparing the value indicative of fluid responsiveness to a fluid responsiveness threshold;
   comparing the value indicative of regional oxygen saturation to a regional oxygen saturation threshold; and
   determining whether to administer fluid to the subject based on both comparisons.

9. The system of claim 8, wherein the regional oxygen saturation threshold is indicative of adequate perfusion of a region associated with the value indicative of regional oxygen saturation.

10. The system of claim 1, wherein the processor is configured to determine the amount of fluid to administer to the subject based on the value indicative of regional oxygen saturation and the value indicative of fluid responsiveness.

11. The system of claim 1, comprising a display configured to display the value indicative of fluid responsiveness and an indication of fluid administration upon a determination to administer fluid to the subject.

12. A physiological monitoring system comprising:
   a monitor configured to receive a first plurality of physiological signals generated by a pulse oximetry sensor coupled to the physiological monitoring system and a second plurality of physiological signals generated by a regional oxygen saturation sensor coupled to the physiological monitoring system, wherein the first plurality of physiological signals are indicative of light detected from a first tissue of a subject and the second plurality of physiological signals are indicative of light detected from a second tissue of the subject, the monitor comprising a processor configured to:
   calculate regional oxygen saturation in the second tissue of the subject based on the second plurality of physiological signals, wherein the second plurality of physiological signals comprise signals from a first detector and a second detector spaced apart from the first detector, and wherein the regional oxygen saturation is calculated based on a differential absorption of light in the second tissue as detected at the first detector relative to the second detector;
   calculate a parameter indicative of fluid responsiveness based on the first plurality of physiological signals; and
   provide an indication to administer fluid to the subject based on the regional oxygen saturation and the parameter indicative of fluid responsiveness.

13. The system of claim 12, wherein the processor is configured to calculate the parameter indicative of fluid responsiveness based on respiratory-induced amplitude variations identified in one of the first plurality of physiological signals.

14. The system of claim 12, wherein the processor is configured to calculate the parameter indicative of fluid responsiveness based on variations of a percent modulation of the first plurality of physiological signals.

15. The system of claim 12, wherein the processor is configured to determine whether to administer fluid to the subject based on the regional oxygen saturation and the parameter indicative of fluid responsiveness.

16. The system of claim 12, wherein the processor is configured to determine an amount of fluid to be administered to the subject based on the regional oxygen saturation and the parameter indicative of fluid responsiveness.

17. The system of claim 12, wherein the processor is configured to determine the effectiveness of fluid administration based on a change in at least one of the regional oxygen saturation and the parameter indicative of fluid responsiveness.

18. The system of claim 17, wherein the processor is configured to control the fluid administration of the subject based on the effectiveness of the fluid administration.

19. The system of claim 12, wherein the second tissue for which regional oxygen saturation is calculated is at least one of the subject's brain, kidney, and abdomen.

20. The system of claim 12, wherein the processor is configured to control the fluid administration of the subject based on the regional oxygen saturation and the parameter indicative of fluid responsiveness.

* * * * *